(12) United States Patent
Rochat et al.

(10) Patent No.: US 8,147,394 B2
(45) Date of Patent: Apr. 3, 2012

(54) CENTRIFUGATION METHOD AND CHAMBER FOR WASHING AND CONTINUOUS SEPARATION OF BLOOD CONSTITUENTS

(76) Inventors: Jean-Denis Rochat, Genolier (CH); Laurent Mosimann, Commugny (CH)

( * ) Notice: Subject to any disclaimer, the term of this patent is extended or adjusted under 35 U.S.C. 154(b) by 794 days.

(21) Appl. No.: 12/280,874

(22) PCT Filed: Feb. 26, 2007

(86) PCT No.: PCT/CH2007/000094
§ 371 (c)(1),
(2), (4) Date: Aug. 27, 2008

(87) PCT Pub. No.: WO2007/098623
PCT Pub. Date: Sep. 7, 2007

(65) Prior Publication Data
US 2009/0050579 A1 Feb. 26, 2009

(30) Foreign Application Priority Data
Feb. 28, 2006 (EP) .................................. 06405087

(51) Int. Cl.
*B04B 7/12* (2006.01)
(52) U.S. Cl. .......................................... 494/27; 494/67
(58) Field of Classification Search .................... 494/12, 494/23–30, 36, 38, 56, 41, 43, 67, 83–85; 210/782
See application file for complete search history.

(56) References Cited

U.S. PATENT DOCUMENTS

| | | | |
|---|---|---|---|
| 4,684,361 A * | 8/1987 | Feldman et al. | 494/41 |
| 4,692,136 A * | 9/1987 | Feldman et al. | 494/38 |
| 4,859,333 A * | 8/1989 | Panzani | 210/360.2 |
| 4,879,031 A * | 11/1989 | Panzani | 210/360.2 |
| 4,943,273 A * | 7/1990 | Pages | 494/41 |
| 4,983,158 A * | 1/1991 | Headley | 494/41 |
| 5,045,048 A * | 9/1991 | Kaleskas et al. | 494/41 |
| 5,141,486 A * | 8/1992 | Antwiler | 494/37 |
| 5,405,308 A * | 4/1995 | Headley et al. | 494/67 |
| 5,445,593 A | 8/1995 | Biesel et al. | |

(Continued)

FOREIGN PATENT DOCUMENTS

JP 59069166 A * 4/1984

(Continued)

OTHER PUBLICATIONS

International Search Report of PCT/CH2007/000094, date of mailing Jun. 26, 2007.

*Primary Examiner* — Charles E Cooley
(74) *Attorney, Agent, or Firm* — Westerman, Hattori, Daniels & Adrian, LLP

(57) ABSTRACT

Centrifugation method and chamber for washing and continuous separation of blood constituents. This chamber comprises at least one first intake channel for the blood, at least one second intake channel for a sterile washing solution, at least one first outlet channel for at least one constituent of this blood, and at least one second outlet channel for a fluid composed of said washing solution and of the other blood constituents. The second intake channel has its downstream end continued on its periphery by a circular deflector. The latter extends into the bottom of the chamber and is terminated along its inner cylindrical side wall by a ridge, which defines a passage of annular cross section for the flow of said sterile washing solution.

17 Claims, 4 Drawing Sheets

U.S. PATENT DOCUMENTS

| | | | |
|---|---|---|---|
| 5,514,070 A * | 5/1996 | Pages | 494/41 |
| 5,882,289 A * | 3/1999 | Sakota et al. | 494/41 |
| 5,971,948 A | 10/1999 | Pages et al. | |
| 6,238,329 B1 * | 5/2001 | Rogers | 494/22 |
| 7,998,052 B2 * | 8/2011 | Chammas | 494/48 |
| 2009/0050579 A1 * | 2/2009 | Rochat et al. | 210/772 |
| 2009/0065424 A1 * | 3/2009 | Rochat | 210/380.3 |

FOREIGN PATENT DOCUMENTS

JP 09192215 A * 7/1997

* cited by examiner

CENTRIFUGATION METHOD AND CHAMBER FOR WASHING AND CONTINUOUS SEPARATION OF BLOOD CONSTITUENTS

BACKGROUND ART

The present invention relates to a centrifugation method and chamber for washing and continuous separation of blood constituents, in particular of red blood cells, from washed blood, intended for auto-transfusion during operations or postoperative bleeding in particular, but also being able to be used for deglycerolization operations, for example.

The technique most commonly used for washing and separating blood constituents is centrifugation. Under the effect of the centrifugal force, the various constituents of the blood separate on account of their different densities. This separation takes place naturally in a predefined order, such that the blood constituent of greater density, namely the red blood cells, is always positioned at the greatest possible distance from the axis of revolution of the chamber, whereas the other natural or added constituents of lower density, such as the plasma or a sterile washing solution, respectively, will always be situated nearer this axis than all the other constituents.

The use of automatic devices for autotransfusion allows the blood lost during or after an operation to be recovered by aspiration using a cannula. The aspirated blood is then mixed with an anti-coagulant solution and is then temporarily stored in a reservoir that filters out the largest undesirable particles such as blood clots, bone debris or organic tissue. It is then pumped into a centrifugation chamber. In a first stage, the red blood cells are concentrated by centrifugation, then washed by injection of a sterile solution, for example a saline solution. The undesirable components such as plasma, waste materials, stromata and the sterile solution are then extracted from the centrifugation chamber after sedimentation and are collected in a bag intended to be disposed of, whereas the washed concentrate of red blood cells is transferred into a re-injection bag serving as a buffer reservoir before being returned to the patient.

Document U.S. Pat. No. 5,445,593 describes a device for washing and separation that permits continuous washing. According to this method, the pumping of the blood into the chamber of the centrifugal separator, the injection of the sterile solution into the pumped blood, the extraction of the waste materials arising from the centrifugation, and the extraction of the blood cell concentrate are operations that are performed simultaneously. The chamber of this device is formed by a spiralling annular channel of rectangular cross section whose two end areas are closed. This channel is subdivided along its length into three zones respectively intended for a first separation of the blood constituents, for mixing these constituents with a washing solution injected into the second zone, and for a second separation during which the blood cell concentrate will be extracted from the chamber. The inlets and outlets used for injection and extraction of the blood, of its constituents and of the washing solution are situated on the outer walls of this chamber, which fact necessitates the provision of tubes turning about the periphery of this chamber in the manner of a lasso. This complicates the structure of the chamber, increases its size and does not make it any easier for medical personnel to prepare and use this device.

Moreover, the injection of the washing solution, as is proposed in this device of the prior art, inevitably creates turbulence which, on the one hand, promotes remixing of the blood constituents that have already been partially separated, and, on the other hand, means that it is not possible to utilize the full cleaning potential of the washing solution. The reason is that, because of its radial injection, its low cross section of injection and its low density, the washing solution tends to pass rapidly through the layer of blood under the effect of the centrifugal force and will finally rise to the surface if the blood flow, positioning itself nearer the axis of rotation than the blood. For these same reasons, the radial movement of this washing solution only takes place locally within a limited area.

SUMMARY OF THE INVENTION

It is an object of the present invention to at least partly overcome the aforementioned disadvantages by proposing a centrifugation method and chamber for washing and continuous separation of blood constituents in a ratio of volume of washing solution to volume of treated red blood cells which is very low, especially by virtue of a good distribution of the flow of the washing solution. Another object is to obtain a centrifugation chamber which is not too large and is easy to use.

To this end, the subject matter of the present invention is a centrifugation method for washing and continuous separation of blood constituents using blood and a sterile washing solution, with a density lower than that of the blood, which are introduced into a centrifugation chamber provided with an inner cylindrical side wall that rotates about an axis of revolution, characterized in that an axial tubular flow of blood with a local thickness is formed against the inner cylindrical side wall, and, between the latter and said axial tubular flow of blood, a film of sterile washing solution is formed with a thickness substantially less than the local thickness, flowing in the same axial direction as the tubular flow of blood in such a way that, under the effect of the centrifugal force, this film gradually passes through the thickness of blood in the direction of the axis of revolution of the chamber. The subject matter of the present invention is also a centrifugation chamber for washing and continuous separation of blood constituents, comprising an inner cylindrical side wall, a bottom with an inner wall, an axis of revolution, and a circular opening provided with a sealing means arranged around a static admission/evacuation member extending into said chamber at least partially along the axis of revolution thereof and comprising at least one first intake channel for the blood, at least one second intake channel for simultaneously conveying a sterile washing solution, at least one first outlet channel for at least one constituent of this blood, and at least one second outlet channel for a fluid composed of said washing solution charged with waste materials and with the other blood constituents, characterized in that the second intake channel has its downstream end continued on its periphery by a circular deflector, which extends in the bottom of the chamber at a distance from the inner wall and is terminated along the inner cylindrical side wall by a ridge which defines, with this wall, a passage of annular cross section for the flow of said sterile washing solution.

This method and this centrifugation chamber advantageously permit a substantial saving in terms of sterile washing solution, thus helping reduce the cost of the medical treatment for which this chamber is intended, and also simplifying the procedures performed by the medical personnel.

BRIEF DESCRIPTION OF THE DRAWINGS

Other advantages will become evident from the following description of a preferred embodiment of the subject matter of the present invention, said embodiment being given as a non-limiting example and being depicted in the attached figures, in which.

DETAILED DESCRIPTION OF PARTICULAR EMBODIMENTS

Figure 1:
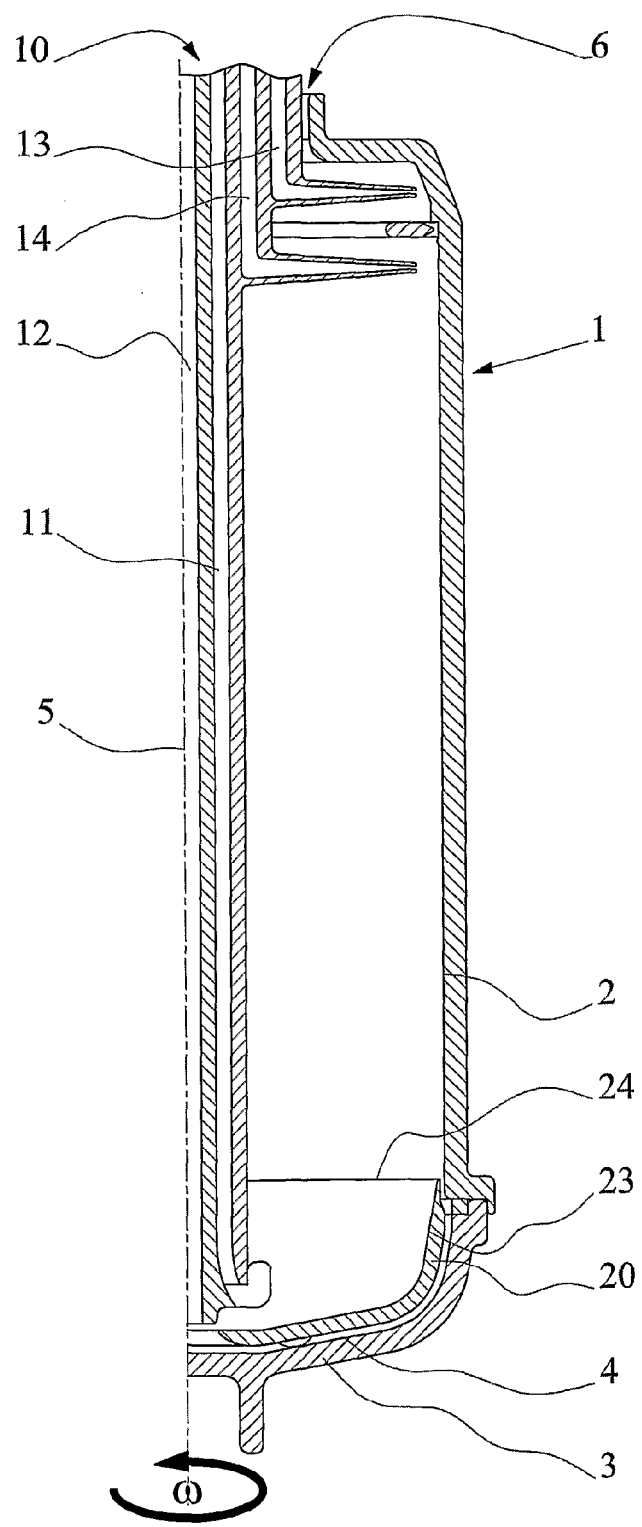
FIG. 1 is a schematic view, in a vertical partial cross section, of the chamber of the present invention, shown without any flow of blood or washing solution.
Figure 2:
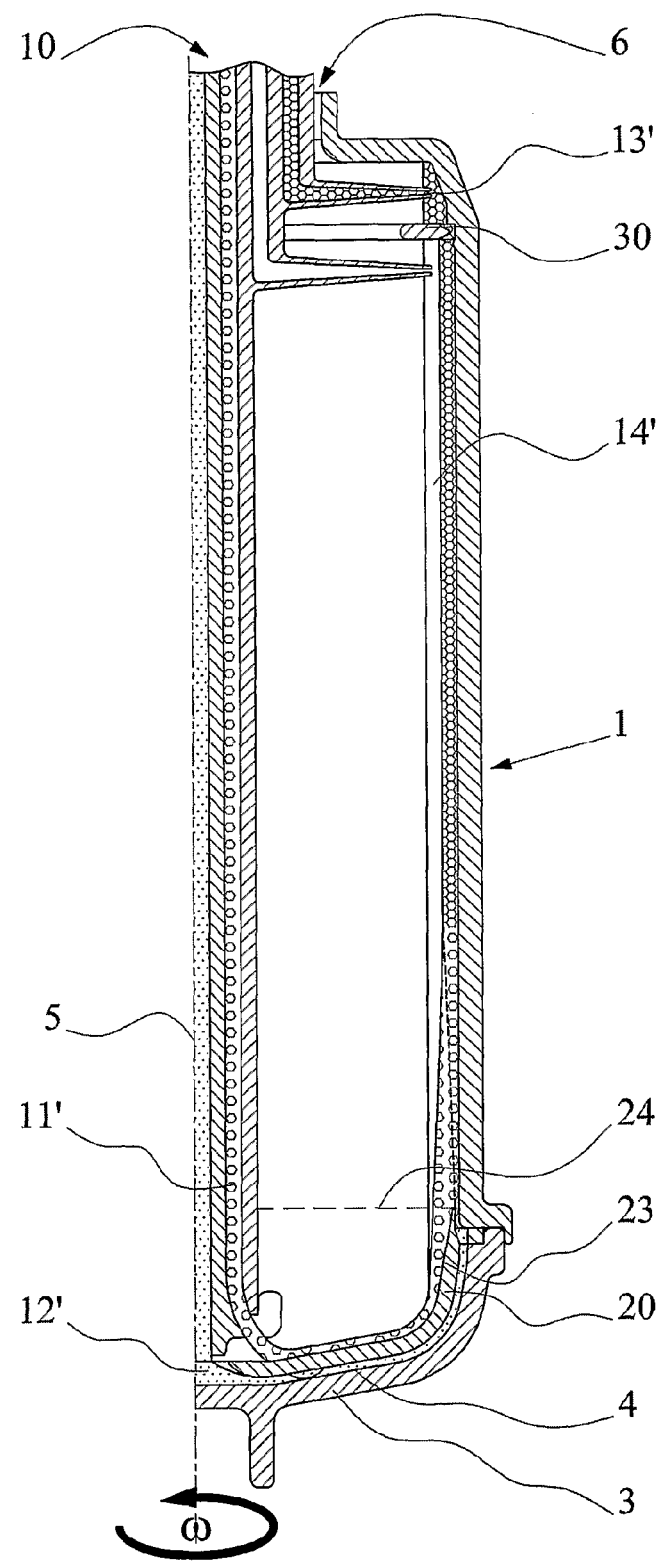
FIG. 2 is a view identical to that of FIG. 1, but in which the flows of blood and of washing solution are depicted under normal conditions of use.

The centrifugation chamber 1, as illustrated in FIGS. 1 and 2, comprises an inner cylindrical side wall 2, a bottom 3 with an inner wall 4, and it preferably has an elongate cylindrical shape about its axis of revolution 5. Its upper end has a circular opening 6 provided with a sealing means (not shown) which can be present in the form of a rotary seal. This sealing means is intended to guarantee sterility inside the chamber by surrounding a static admission/evacuation member 10 that extends into the chamber, at least partially along the axis of revolution 5 thereof.

The fixed part formed by this static member 10 comprises a plurality of conduits permitting easy exchange of fluids between the inside and outside of the centrifugation chamber. Among the conduits intended to convey fluids into the chamber, provision is made for the static member 10 to comprise at least one first intake channel 11 for entry of blood 11' into the chamber, and at least one second intake channel 12 for simultaneous entry of a sterile washing solution 12', for example a saline solution. To be able to extract these fluids from the chamber once they have been treated, and to permit a continuous circulation of the blood flow, the static member 10 is also provided with at least one first outlet channel 13 for at least one constituent 13' of this blood, such as a concentrate of washed red blood cells, and at least one second outlet channel 14 for extracting from the chamber a fluid 14' composed, on the one hand, of the other blood constituents, for example plasma, and, on the other hand, of the washing solution charged with waste matter originating from the treated blood.

According to the preferred embodiment of the invention, the first intake channel 11, intended for introduction of the blood 11' to be treated, has an annular shape surrounding the second intake channel 12. The intake channels 11 and 12 are preferably concentric, and the second intake channel is situated on the axis of rotation 5 of the chamber. The downstream ends of these two channels are situated near the bottom 3 of this chamber, more precisely near the inner wall 4 of this bottom.

The downstream end of the second intake channel 12 is continued on its periphery by a circular deflector 20 which extends, at a distance from the inner wall 4, in the bottom 3 of the chamber. This circular deflector 20 constitutes, for the centrifugation chamber, a sort of double bottom extending substantially parallel to the inner wall 4 before ascending, on its outer edge, partially along the inner cylindrical side wall 2.

Figure 4:
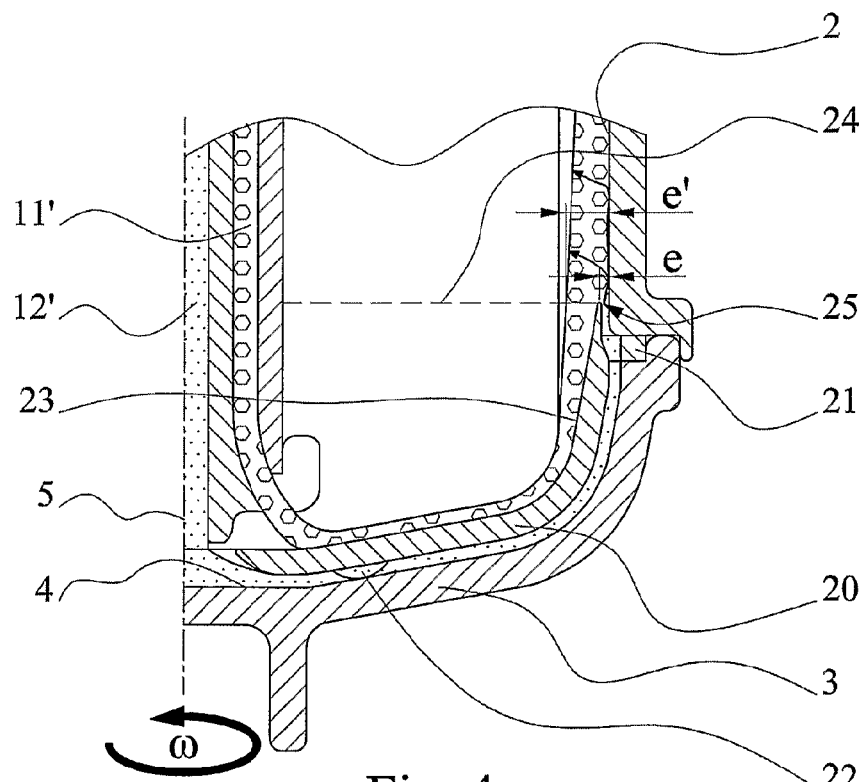
Figure 5:
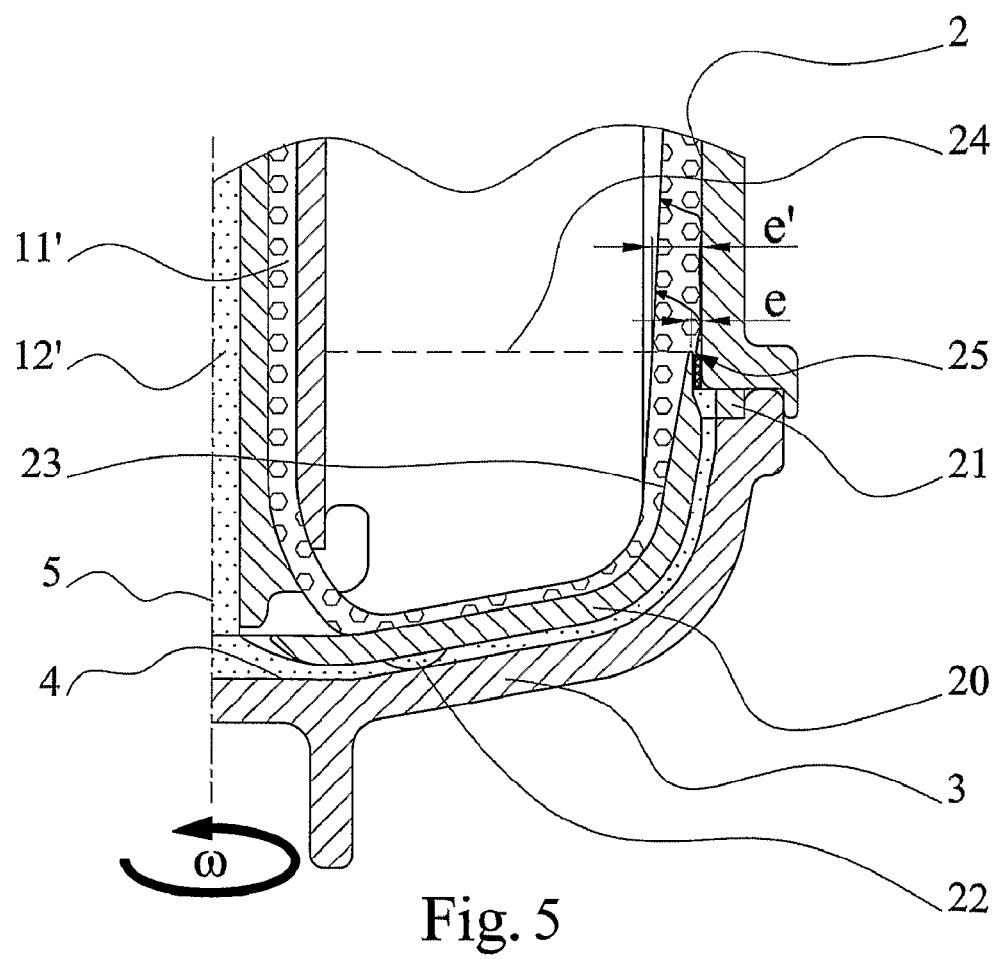
FIG. 5 corresponds to FIG. 4 with a ring of porous material forming a passage of annular cross section.

According to the preferred embodiment, and as can be better seen in FIG. 4 which illustrates in detail the lower part of the chamber depicted in FIG. 2, the bottom 3 of this chamber constitutes the lower part thereof, and it is connected integrally to the foot of the side wall 2 by a customary assembly system, for example by interlocking, by a clip fit or by welding. The benefit of this assembly system is that it can also be used for insertion of securing fins 21 for holding the cylindrical deflector 20 in its position as described above. Toward its downstream end, this deflector rests on a plurality of humps 22 distributed uniformly about its circumference. These humps serve as support points and are preferably as thin as possible so as not to disturb the flow of the sterile washing liquid 12'. The circular deflector 20 is intended, together with the inner wall 4 of the bottom 3 of the chamber, to define a passage for the flow of the sterile washing solution 12' separate from that of the blood 11'. The latter flows on the upper face 23 of the deflector 20 and finds itself applied instantaneously thereto under the effect of the centrifugal force acting on this fluid.

At its downstream end, the circular deflector 20 is terminated along the inner cylindrical side wall 2 by a ridge 24 which, with this wall, defines a passage of annular cross section 25 for the flow of said sterile washing solution. This ridge constitutes the end of a spout of the circular deflector 20. It is preferably situated at a level located in the first lower quarter of the height of the centrifugation chamber. As can be better seen from FIG. 4, this passage of annular cross section 25 has a thickness e substantially less than the local thickness e' of the layer of blood 11' rotating in the chamber 1 at the level of said ridge 24. Preferably, this passage of annular cross section has a thickness of between 0.02 mm and 2 mm, and the level of the ridge 24 is at a distance of 5 to 50 mm away from the level of the downstream end of the second intake channel 12.

By virtue of this embodiment, the injection of the flow of sterile washing solution 12' advantageously takes place in the same direction as the ascending current of the blood 11'. Moreover, this injection takes place at the periphery of the flow of blood, namely along the inner cylindrical side wall 2 of the chamber. For this reason, the vortices and remixing that could be caused by such an injection within the already partially sedimented layer of blood are reduced as far as possible. This makes it possible to avoid any formation of bypasses in the layer of blood, namely any formation of bridges of sterile solution that would cross the thickness of this layer and would short-circuit the washing effect that one aims to optimize upon injection of this solution.

The formation of bypasses is also linked to the speed of penetration of the flow of washing solution at the periphery of the layer of blood in the centrifugation chamber. If this speed is low, then the thickness of the layer of washing solution, corresponding to the thickness e of the passage of annular cross section 25, will necessarily be increased and the risks of bypasses will be greater. By contrast, if the speed of penetration of the flow of washing solution is high, and the thickness e is consequently small, then the same volume of washing solution will be distributed over a greater surface area of the blood to be washed, and this will reduce the risk of formation of bypasses.

Besides the absence of formation of bypasses, for the reasons explained above, the ratio between the volume of washing solution and the volume of treated red blood cells is further improved by the fact that the thickness e of the second passage of annular cross section 25 is very fine, and this passage makes it possible to create a sort of thin stream or annular film of sterile washing solution, which is initially applied against the inner cylindrical side wall of the chamber at the level of the ridge 24 of the deflector. The surface/thickness ratio of the sterile washing solution on the inner cylindrical side wall 2 is preferably very high.

During centrifugation, three simultaneous effects will be produced. On the one hand, the sterile washing solution injected in the form of a uniform annular film of low thickness e will, under the effect of the centrifugal force, pass through the thickness e' of the blood flow 11' along its full length and will carry with it the impurities until this solution is located again at the surface of the blood thus washed. On the other hand, the plasma will be pushed in the direction of the center of the centrifugation chamber, driven by the concentric movement of this washing solution. Finally, the simultaneous sedimentation of the red blood cells will accelerate the cross-flow effect obtained between the washing solution and the red blood cells.

This migration of the sterile washing solution will take place gradually, starting at the downstream outlet of the deflector 3 and ending higher up, near to the middle or upper part of the height of the chamber, but in all cases before reaching the level of the lowest of the collectors connected to the outlet channels 13, 14. Thus, the washing solution will as it were be able to filter the blood flow applied against the side wall of the chamber by passing through the full thickness thereof. In this way, any formation of bypasses will be avoided, and the washing effect of the sterile solution will be optimized. The abovementioned ratio of this solution will thereby be optimized.

Figure 3:
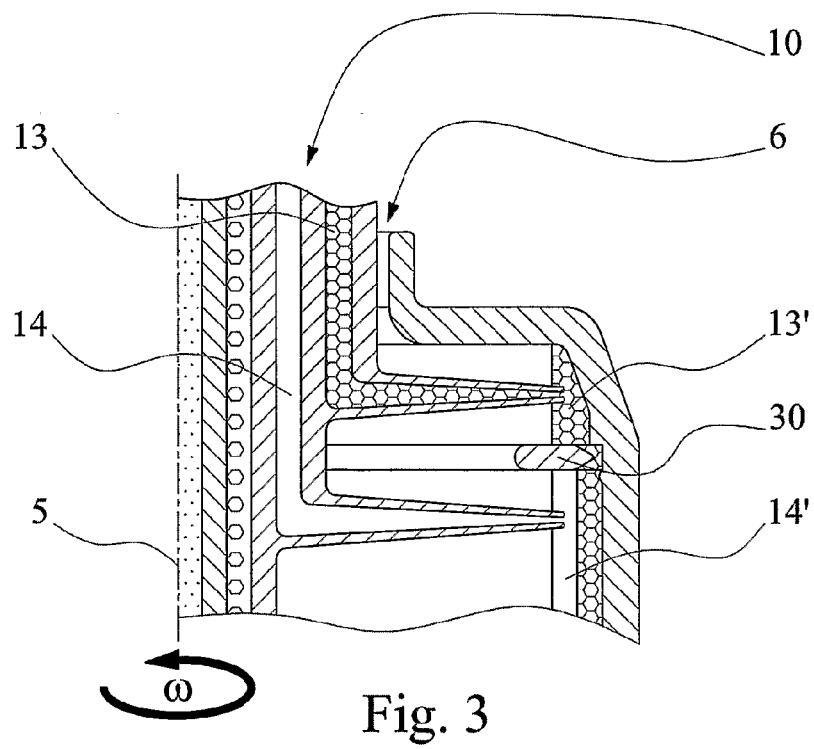
FIGS. 3 and 4 show details of FIG. 2, namely of its upper part and of its lower part, respectively.

Referring to FIG. 3, the latter shows in detail the upper part of the chamber 1 as illustrated in FIG. 2. At this level, the sedimentation of the blood 11' resulting from the centrifugal effect is terminated, as is its washing by means of the sterile solution 12'. This blood 11' initially charged with impurities will be separated into at least two distinct layers of fluids 13' and 14', respectively situated against the inner cylindrical side wall 2 of the chamber and at a distance nearer to the axis of revolution of this chamber. The first fluid 13' of greater density corresponds to the concentrate of red blood cells which, for example, will be re-injected into the patient according to the principle of autotransfusion, whereas the second fluid 14' of lower density comprises the other blood constituents, at least the plasma, and all the waste materials that have been withdrawn from the blood 11' by the sterile washing solution.

The blood cell concentrate 13' is extracted from the chamber, at the highest part thereof, by means of a collector that constitutes the final part of the upstream end of the first outlet channel 13. It is then collected in an intermediate storage bag (not shown) serving as a buffer volume before being re-injected into the patient. In a similar way, the fluid 14' is extracted from the chamber by means of another collector situated at the upstream end of the second outlet channel 14 and is finally collected in a bag (not shown), which will be disposed of. The upstream ends of these collectors are immersed within the thickness of each layer of fluid for which these collectors are intended.

According to a preferred embodiment, a circular barrage 30, preferably in the form of a flat ring concentric to the axis of revolution of the centrifugation chamber, is arranged between the collectors of the outlet channels 13, 14 in order to prevent re-mixing of the two fluids 13', 14' during their extraction. For this purpose, the external diameter of this circular barrage 30 is greater than the diameter of the interface between the layer of red blood cells 13', which is the layer farthest from the axis of revolution of the chamber, and the layer of the fluid 14' composed of the other blood constituents and of the washing solution 12' charged with waste matter. The internal diameter of such an annular barrage is smaller than the internal diameter of the layer of fluid 14' nearest to the axis of revolution of the chamber. By virtue of the divide that this barrage constitutes, the collectors of the outlet channels 13 and 14 are able to function independently, such that the possible flow disturbances created by one do not affect the other.

The flow rate of admission of the blood 11' into the centrifugation chamber 1 is preferably regulated as a function of its hematocrit level, in such a way that the incoming flow of red blood cells is constant. This regulation (not shown) can be effected by a pumping means or by a control valve, and it is governed by a measurement of the hematocrit level of the blood 11' upstream of the centrifugation chamber.

It is also preferable for the flow of the sterile washing solution 12' to be continuous and proportional to the interstitial outlet flow of the washed and re-concentrated red blood cells 13'. Typically, the flow rate of the washing solution can be in a range of between 1 and 10 times that of the flow of treated red blood cells.

According to another possible embodiment, the ridge 24 of the circular deflector 20 is situated at a level located in the lower third or lower half of the height of the centrifugation chamber. In this way, the sterile washing solution 12' will be re-injected into a layer of blood 11' which has a smaller local thickness e' but which will advantageously be at a more advanced stage of sedimentation. For this reason, this layer will comprise at this level a greater concentration of red blood cells, which will necessitate a smaller quantity of washing solution. In this connection, however, it should be noted that the injection of the sterile washing solution in the form of an annular film requires a certain fluidity of the body of red blood cells in order to avoid this film being dislocated too early and thus generating the formation of bypasses. Thus, the level at which the ridge 24 must be situated in order to optimize the efficiency of the sterile washing solution will be the result of a compromise in particular between the viscosity of the partially sedimented cell mass of the blood 11' and the thickness of the film of washing solution in line with this ridge. This thickness corresponds to the thickness e of the passage of annular cross section 25.

According to another embodiment not shown here, the passage of annular cross section 25 could be formed by a ring, crown or annulus of porous material, of which the opening of the pores would preferably be too small to permit passage of the red blood cells, but sufficiently large to permit the passage of the sterile washing solution. The arrangement of a ring made of porous material at the site corresponding to the passage of annular cross section 25 would make it possible to lengthen the contact surface between the sterile washing solution and the blood or the concentrate of red blood cells.

The dimensions of the centrifugation chamber are of the order of 50 to 200 mm in height, with a diameter of between 15 and 150 mm approximately.

The method of the present invention derives from the principle of the cross-flow effect obtained between the washing solution and the red blood cells. This method is intended for the washing and continuous separation of blood constituents using blood 11' and a sterile washing solution 12'. With a density lower than that of the blood 11', this solution is introduced, with the blood 11', into the centrifugation chamber 1. The inner cylindrical side wall 2 of this chamber 1 is in rotation about the axis of revolution 5.

According to the invention, an axial tubular flow of blood 11' is formed with a local thickness e' against the inner cylindrical side wall 2. A film of sterile washing solution 12' with a thickness e' substantially less than the local thickness e is also formed between this inner cylindrical side wall 2 and the axial tubular flow of blood 11'. This film flows continually in the same axial direction as the tubular flow of blood 11', in such a way that, under the effect of the centrifugal force, it gradually passes through the thickness e' of blood 11' in the direction of the axis of revolution 5 of the chamber 1. Thus, the radial movement of this film takes place from its contact with the inner cylindrical side wall 2 and continues until the surface of the tubular flow of blood 11' nearest to the axis of revolution 5. The direction of the axial tubular flow of blood 11' is preferably upward, and the film of sterile washing solution is then obtained by injecting the latter in this upward direction, at the surface of the inner cylindrical side wall 2.

The invention claimed is:

1. A method for washing and continuous separation of blood constituents using blood and a sterile washing solution, with a density lower than that of the blood, which are introduced into a centrifugation chamber provided with an inner cylindrical side wall that rotates about an axis of revolution, characterized in that an axial tubular flow of blood with a local thickness is formed against the inner cylindrical side wall, and, between the latter and said axial tubular flow of blood, a film of sterile washing solution is formed with a thickness substantially less than the local thickness, flowing in the same axial direction as the tubular flow of blood in such a way that, under the effect of the centrifugal force, this film gradually passes through the thickness of blood in the direction of the axis of revolution of the chamber.

2. A centrifugation chamber for washing and continuous separation of blood constituents, comprising an inner cylindrical side wall, a bottom with an inner wall, an axis of revolution, and a circular opening provided with a sealing means arranged around a static admission/evacuation member extending into said chamber at least partially along the axis of revolution thereof and comprising at least one first intake channel for the blood, at least one second intake channel for simultaneously conveying a sterile washing solution, at least one first outlet channel for at least one constituent of this blood, and at least one second outlet channel for a fluid composed of said washing solution charged with waste materials and with the other blood constituents, characterized in that the second intake channel has its downstream end continued on its periphery by a circular deflector, which extends in the bottom of the chamber at a distance from the inner wall and is terminated along the inner cylindrical side wall by a ridge which defines, with this wall, a passage of annular cross section for the flow of said sterile washing solution.

3. The centrifugation chamber as claimed in claim 2, wherein the first intake channel is annular and surrounds the second intake channel.

4. The centrifugation chamber as claimed in claim 3, wherein the first and second intake channels are concentric.

5. The centrifugation chamber as claimed in claim 4, wherein the passage of annular cross section is formed by a ring made of porous material.

6. The centrifugation chamber as claimed in claim 3, wherein the passage of annular cross section is formed by a ring made of porous material.

7. The centrifugation chamber as claimed in claim 2, wherein the passage of annular cross section has a thickness substantially less than the local thickness of a layer of blood rotating in the chamber at the level of said ridge.

8. The centrifugation chamber as claimed in claim 7, wherein the passage of annular cross section has a thickness of between 0.02 mm and 2 mm.

9. The centrifugation chamber as claimed in claim 8, wherein the passage of annular cross section is formed by a ring made of porous material.

10. The centrifugation chamber as claimed in claim 7, wherein the level of said ridge is 5 to 50 mm away from that of the downstream end of the second intake channel.

11. The centrifugation chamber as claimed in claim 10, wherein the passage of annular cross section is formed by a ring made of porous material.

12. The centrifugation chamber as claimed in claim 7, wherein the passage of annular cross section is formed by a ring made of porous material.

13. The centrifugation chamber as claimed in claim 2, wherein that the ridge (24) of the circular deflector is situated at a level located in the lower half of the height of the centrifugation chamber.

14. The centrifugation chamber as claimed in claim 13, wherein the ridge of the circular deflector is situated at a level located in the lower quarter of the height of the centrifugation chamber.

15. The centrifugation chamber as claimed in claim 14, wherein the passage of annular cross section is formed by a ring made of porous material.

16. The centrifugation chamber as claimed in claim 13, wherein the passage of annular cross section is formed by a ring made of porous material.

17. The centrifugation chamber as claimed in claim 2, wherein the passage of annular cross section is formed by a ring made of porous material.

* * * * *